United States Patent [19]

Scriabine

[11] 4,389,415
[45] Jun. 21, 1983

[54] METHOD OF TREATING HYPERTENSION

[75] Inventor: Alexander Scriabine, Ambler, Pa.

[73] Assignee: Merck & Co., Inc., Rahway, N.J.

[21] Appl. No.: 285,215

[22] Filed: Jul. 20, 1981

Related U.S. Application Data

[63] Continuation of Ser. No. 82,249, Oct. 5, 1979, abandoned, which is a continuation of Ser. No. 871,879, Jan. 24, 1978, abandoned.

[51] Int. Cl.³ .................... A61K 31/24; A61K 31/195
[52] U.S. Cl. ..................................... 424/309; 424/319
[58] Field of Search ................ 424/308, 309, 317, 319

[56] References Cited

U.S. PATENT DOCUMENTS

| | | | |
|---|---|---|---|
| 3,344,023 | 9/1967 | Reinhold | 424/319 |
| 3,462,536 | 8/1969 | Chemerda | 424/309 |
| 3,781,415 | 12/1973 | Karady | 424/308 |
| 3,830,827 | 8/1974 | Karady | 260/471 A |
| 3,839,585 | 10/1974 | Lotti | 424/319 |
| 3,883,656 | 5/1975 | Hedwall | 424/319 |
| 4,065,572 | 12/1977 | Atkinson | 424/273 R |

FOREIGN PATENT DOCUMENTS

| | | | |
|---|---|---|---|
| 737907 | 7/1966 | Canada | 424/319 |

OTHER PUBLICATIONS

Shalita, Experientia, vol. 33, 1977, pp. 1430–1431.
Spector, J. Pharmacol. Exptl. Therap., vol. 147, 1965, pp. 86–95.
Engelman, J. Clin. Invst. vol. 47, 1968, pp. 568–594.
Sjoerdsma, The Lancet, 2, Nov. 27, 1965, pp. 1092–1094.

*Primary Examiner*—Anna P. Fagelson
*Attorney, Agent, or Firm*—Salvatore C. Mitri; Daniel T. Szura

[57] ABSTRACT

A pharmaceutical composition containing α-methyl-p-tyrosine and carbidopa and method of treating hypertension are described.

2 Claims, No Drawings

METHOD OF TREATING HYPERTENSION

This is a continuation of Ser. No. 82,249, filed Oct. 5, 1979 which in turn is a continuation of U.S. Ser. No. 871,879, filed Jan. 24, 1978, both now abandoned.

BACKGROUND OF THE INVENTION

The present invention is directed to pharmaceutical compositions containing L-α-methyl-p-tyrosine and a decarboxylase inhibitor and method of treating hypertension.

L-α-methyl-p-tyrosine is known to be useful as an antihypertensive agent. The present decarboxylase inhibitor is encompassed in the class of hydrazino phenyl propionic acid compounds disclosed in U.S. Pat. No. 3,462,536; U.S. Pat. No. 3,830,827 and U.S. Pat. No. 3,781,415. Combinations of this hydrazino phenylpropionic acid type decarboxylase inhibitor with α-methyl-m-tyrosine, m-tyrosine and L-tyrosine are disclosed in Canadian Pat. No. 737,907, U.S. Pat. No. 3,839,585 and Shalita et al, Experientia 33, 1430–1431 (1977), respectively.

It has now been discovered that the combination of L-α-methyl-p-tyrosine and the hydrazino-phenyl propionic acid type decarboxylase inhibitors affords enhanced anti-hypertensive activity.

SUMMARY OF THE INVENTION

Pharmaceutical compositions comprising (a) L-α-methyl-p-tyrosine and (b) a D,L- or L-hydrazino-phenyl propionic acid decarboxylase inhibitor and method of treating hypertension.

DESCRIPTION OF THE PREFERRED EMBODIMENTS

An embodiment of this invention is a hypotensive pharmaceutical compositions comprising
(a) L-α-methyl-p-tyrosine of the formula:

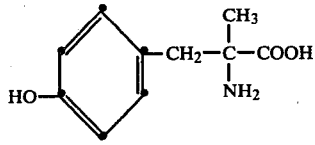

or a pharmaceutically acceptable salt thereof and (b) the L-isomer or racemic mixture (D,L-) of a hydrazino phenylpropinic acid decarboxylase inhibitor, or a pharmaceutically acceptable salt thereof. The compositions are useful for treating hypertension (high blood pressure) in hypertensive patients, including humans.

Preferred decarboxylase inhibitors include the D,L-racemic mixture and the individual L-isomer of compounds having the formula:

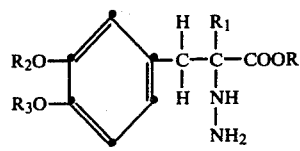

wherein R, $R_1$, $R_2$ and $R_3$ are independently selected from hydrogen and $C_1$–$C_4$ alkyl such as methyl, t-butyl, isopropyl and the like. A more preferred decarboxylase inhibitor is the L-isomer and most preferred is the L-isomer of

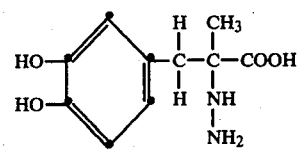

and its pharmaceutically acceptable salts. The monohydrate of III is known as carbidopa. A most preferred composition comprises (a) L-α-methyl-p-tyrosine and (b) carbidopa.

Pharmaceutically acceptable salts include the salts of the various compounds with suitable organic or inorganic acids. Suitable organic acids are $C_2$–$C_{24}$ carboxylic acids such as acetic acid, maleic acid, pamoic acid, succinic acid, citric acid, propionic acid, oxalic acid, pivalic acid and the like; and isethionic acid. Suitable inorganic acids include the hydrohalides, e.g. HCl, HI, HBr, sulfuric acid, phosphoric acid and the like.

The compositions of the present invention may contain varying amounts of the L-α-methyl-p-tyrosine and decarboxylase inhibitor. In general, the weight ratio of L-α-methyl-p-tyrosine (a) to decarboxylase inhibitor (b) will range from about 4:1 to about 1:400. A preferred weight ratio of (a):(b) is about 4:1 to about 1:160; a more preferred ratio is about 3:1 to about 1:80 and an especially preferred ratio is about 3:1 to about 1:20.

In treating hypertension, a sufficient amount of the present composition is administered to the hypertensive patient to produce the desired hypotensive effect i.e. reduction in blood pressure. Effective dosages for humans will vary and may range from about 50 mg to about 2000 mg per day. Preferred daily dosages may range from about 400–800 mg. The composition may be given as a single daily dose or divided into several smaller doses during the course of the day.

The composition may be administered parenterally or orally. The dosage form used will depend on the mode of administration. The oral form may be a tablet, a liquid solution, dispersion, or emulsion, a capsule, or an encapsulated composition—while the parenteral dosage form will generally be a liquid solution, suspension or emulsion. The dosage forms generally will include conventional carriers, diluents, either solid or liquid, dyes etc. and will be prepared using applicable formulation procedures.

Additionally, the present composition may be administered using a system and/or device designed to intermittently or continuously deliver the present compositions to the hypertensive patient.

Following are formulations of some representative dosage forms:

| Tablet Formulation | |
|---|---|
| L-α-methyl-p-tyrosine | 0.1 mg |
| Carbidopa | 5.0 mg |
| Calcium phosphate | 50.0 mg |
| Lactose | 20.0 mg |
| Starch | 10.0 mg |
| Magnesium sulfate | 0.5 mg |
| Liquid Suspension | |
| L-α-methyl-p-tyrosine | 2.5 g |
| Carbidopa | 2.5 g |
| Veegum HV | 3.0 g |
| Methylparaben | 1.0 g |
| Kaolin | 10.0 g |

| -continued | |
|---|---|
| Glycerin | 250.0 g |
| Water, q.s. → 1 liter | |
| Injectable Solution | |
| L-α-methyl-p-tyrosine.HCl | 20 mg |
| Carbidopa.HCl | 100 mg |
| Distilled water, q.s. → 1 ml | |
| Capsule Formulation - I | |
| L-α-methyl-p-tyrosine | 50 mg |
| Carbidopa | 15 mg |
| Lactose | 50 mg |
| Talc | 3 mg |
| Capsule Formulation - II | |
| L-α-methyl-p-tyrosine | 0.2 mg |
| Carbidopa | 100.0 mg |
| Mannitol | 98.0 mg |
| Stearic acid | 1.0 mg |

Another embodiment of the present invention is method of treating hypertensive patients by administering an antihypertensive effective amount of (a) L-α-methyl-p-tyrosine and (b) the aforesaid decarboxylase inhibitor. The daily dosage and the weight ratio of (a):(b) is the same as that described above for the composition. Carbidopa is a preferred decarboxylase inhibitor.

The method of treatment may conveniently be carried out by administering a composition described above containing both the (a) and (b) components in a single dosage form.

Treatment may also be effected by administering the (a) and (b) components separately, and either simultaneously or consecutively. The simultaneous but separate administration may be achieved e.g. by having the patient take two separate tablets one containing (a) and one containing (b), by injecting one component and taking the other orally as by injecting each component.

The consecutive method of treatment will involve administration of either the (a) or (b) compound first followed by the second compound. It is preferred that the (b) compound, e.g. carbidopa, be administered first. The time interval between the administration of the first component and the second component may be varied.

The use of the present method and/or composition effect an unexpected reduction in blood pressure in hypertensive patients. The decarboxylase inhibitors are known to have no appreciable anti-hypertensive effect. L-α-methyl-p-tyrosine can be expected to lower blood pressure, in patients with essential hypertension, only at relatively high doses—and these required high doses may cause kidney stones to form. Thus, using the present compositions/method of treatment, hypertension is effectively controlled and the undesirable side effect (kidney stone formation) may be minimized or eliminated.

The enhancement of antihypertensive activity is demonstrated in vivo in spontaneously hypertensive (SH) rats. The test procedure used is substantially as follows:

The test animals used were conscious, male, SH rats weighing about 290 to about 340 grams. The arterial blood pressure was measured by a direct technique involving cannulation of the caudal artery. Initial blood pressure reading was recorded. The decarboxylase inhibitor was then administered intraperitoneally (i.p.) and about 5 minutes later the L-α-methyl-p-tyrosine was given [(i.p. or orally (p.o.)]. The blood pressure was then continuously recorded at ½ hour intervals for 24 hours.

The effect on blood pressure of the decarboxylase inhibitor and the L-α-methyl-p-tyrosine alone was also obtained by this test method. The results of representative tests are in the following table:

TABLE

Effect of α-methyl-p-tyrosine, alone and in combination with carbidopa, on mean arterial pressure of conscious SH rats.

| Test No. | Treatment[1] | Dose (mg/kg) | Route | No. of Rats | Mean arterial pressure, mm Hg, at hours after treatment | | | | | | | | |
|---|---|---|---|---|---|---|---|---|---|---|---|---|---|
| | | | | | 0 | ½ | 1 | 2 | 4 | 8 | 12 | 18 | 24 |
| 1 | Saline | 2[2] | i.p. | 9 | 168 | 170 | 170 | 170 | 166 | 164 | 166 | 166 | 164 |
| 2 | Carbidopa | 25 | i.p. | 6 | 167 | 166 | 164 | 166 | 158 | 167 | 172 | 172 | 162 |
| 3 | α-methyl-p-tyrosine | 5 | i.p. | 7 | 165 | 155 | 162 | 160 | 161 | 167 | 164 | 168 | 164 |
| 4 | α-methyl-p-tyrosine | 20 | i.p. | 6 | 165 | 152 | 159 | 157 | 146 | 156 | 155 | 161 | 166 |
| 5 | α-methyl-p-tyrosine | 40 | i.p. | 6 | 166 | 148 | 152 | 145 | 135 | 140 | 134 | 130 | 135 |
| 6 | α-methyl-p-tyrosine | 80 | i.p. | 6 | 167 | 166 | 158 | 146 | 138 | 131 | 130 | 136 | 130 |
| 7 | Carbidopa + α-methyl-p-tyrosine | 25 0.078 | i.p. | 6 | 174 | 166 | 169 | 169 | 168 | 163 | 165 | 166 | 175 |
| 8 | Carbidopa + α-methyl-p-tyrosine | 25 0.156 | i.p. | 6 | 171 | 162 | 159 | 160 | 165 | 160 | 162 | 165 | 165 |
| 9 | Carbidopa + α-methyl-p-tyrosine | 25 0.312 | i.p. | 6 | 166 | 156 | 156 | 153 | 155 | 146 | 149 | 148 | 163 |
| 10 | Carbidopa + α-methyl-9-tyrosine | 25 1.25 | i.p. | 6 | 172 | 155 | 149 | 151 | 157 | 165 | 163 | 169 | 172 |
| 11 | dilute HCl[3] | 2[2] | i.p. | 7 | 179 | 185 | 183 | 185 | 181 | 176 | 170 | 168 | 178 |
| 12 | dilute HCl[3] | 2[2] | p.o. | 3 | 170 | 167 | 167 | 163 | 159 | 161 | 159 | 166 | 165 |
| 13 | Carbidopa | 25 | i.p. | 12 | 184 | 184 | 180 | 178 | 177 | 184 | 183 | 185 | 182 |
| 14 | α-Methyl-p-tyrosine | 80 | p.o. | 4 | 169 | 165 | 166 | 161 | 143 | 147 | 161 | 165 | 173 |
| 15 | Carbidopa | 25 | i.p. | 6 | 176 | 168 | 164 | 164 | 142 | 128 | 120 | 124 | 139 |

TABLE-continued

Effect of α-methyl-p-tyrosine, alone and in combination with carbidopa, on mean arterial pressure of conscious SH rats.

| Test No. | Treatment[1] | Dose (mg/kg) | Route | No. of Rats | Mean arterial pressure, mm Hg, at hours after treatment | | | | | | | |
|---|---|---|---|---|---|---|---|---|---|---|---|---|
| | | | | | 0 | ½ | 1 | 2 | 4 | 8 | 12 | 18 | 24 |
| | + α-Methyl-p-tyrosine | 80 | p.o. | | | | | | | | | | |

[1] test compounds were administered dissolved in dilute HCl, the α-methyl-p-tyrosine is the L-isomer
[2] ml/kg
[3] 1 ml 1NHCl diluted to 10 ml with water.

The data in the table clearly shows the substantial antihypertensive effect obtained with the combination of α-methyl-p-tyrosine and carbidopa. While the test data were obtained using separate but consecutive administration of the carbidopa/α-methyl-p-tyrosine, comparable results are also achieved by (1) simultaneous and separate administration of the two compounds (2) administration of the single composition containing the two compounds or (3) metered administration of the two compounds via a device or system provided to the patient e.g. by implantation, attachment, ingestion etc. Similar results are obtained when other decarboxylase inhibitors disclosed herein are used in place of the carbidopa. The test results also indicate that the present method and composition will be useful for treating hypertension in humans.

Claims to the invention follow.

What is claimed is:

1. A method of treating hypertension which comprises consecutively administering to a hypertensive patient in an antihypertensively effective ratio an effective amount therefor first of (a) racemic mixture of L-isomer of a hydrazino phenylpropionic acid decarboxylase inhibitor of the formula

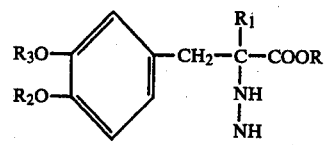

wherein R, $R_1$, $R_2$, and $R_3$ are independently selected from hydrogen and $C_1$–$C_4$ alkyl or a pharmaceutically acceptable salt thereof and then an effective amount therefor of (b) α-methyl-p-tyrosine, with (a) being administered parenterally and (b) being administered orally.

2. The method of claim 1 wherein said decarboxylase inhibitor (a) is carbidopa and the weight ratio of (a):(b) is about 1:4 to about 400:1.

* * * * *